United States Patent
Daw et al.

(10) Patent No.: US 6,245,044 B1
(45) Date of Patent: *Jun. 12, 2001

(54) VARIABLE EXTENSION COMBINED SPINAL/EPIDURAL NEEDLE SET AND METHOD FOR ITS USE

(75) Inventors: Sean P. Daw, Chicago, IL (US); Ronald W. Marsh, Sparta, NJ (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/118,269

(22) Filed: Jul. 17, 1998

(51) Int. Cl.[7] .................................. A61M 5/178
(52) U.S. Cl. ..................... 604/158; 604/164; 604/165; 604/264; 604/272
(58) Field of Search ................. 604/158–167, 604/256, 264, 272–274

(56) References Cited

U.S. PATENT DOCUMENTS

| | | | |
|---|---|---|---|
| 5,085,631 | * 2/1992 | Leighton | 604/28 |
| 5,312,351 | 5/1994 | Gerrone | 604/117 |
| 5,312,375 | * 5/1994 | Gurmarnik | 604/264 |
| 5,368,573 | 11/1994 | Andrew | 604/158 |
| 5,429,616 | 7/1995 | Schaffer | 604/250 |
| 5,480,389 | 1/1996 | McWha, et al. | 604/165 |
| 5,584,820 | * 12/1996 | Gurmarnik | 604/158 |
| 5,725,504 | 3/1998 | Collins | 604/165 |
| 5,836,914 | 11/1998 | Houghton | 604/117 |
| 5,871,470 | 2/1999 | McWha | 604/158 |

FOREIGN PATENT DOCUMENTS

| | | | |
|---|---|---|---|
| 295 03 750 | 4/1995 | (DE) | A61M/25/01 |
| EP 0 696 437 A2 | 2/1996 | (EP) | A61B/17/34 |
| EP 0 761 173 A2 | 3/1997 | (EP) | A61B/17/34 |
| 0 824 894 A1 | 2/1998 | (EP) | A61B/17/34 |
| 2 309 170 A | 7/1997 | (GB) | A61B/17/34 |

OTHER PUBLICATIONS

Copy of European Search Report from corresponding European patent application.
Literature on B. Braun CSE Espocan Device.

* cited by examiner

*Primary Examiner*—Wynn Wood Coggins
*Assistant Examiner*—Deborah Blyveis
(74) *Attorney, Agent, or Firm*—Eric M. Lee, Esq.

(57) ABSTRACT

An epidural needle has an elongate tube defining a longitudinal axis having a proximal end, a distal end and an axial hollow bore having an inside diameter therethrough. The needle has a hub with a proximal end, a distal end and an open passageway having an inside diameter substantially similar to the hollow bore therethrough, the distal end of the hub being fixedly attached to the proximal end of the elongate tube so that the hollow bore of the elongate tube is in fluid communication and substantial axial alignment with the open passageway. The hub further has a cavity disposed between the proximal end and the distal end of the hub. There is a resilient member with an opening therethrough that has an inner diameter substantially similar to the inside diameter of the hollow bore disposed in the cavity so that the opening is substantially axially aligned and in fluid communication with the open passageway. The hub of the epidural needle of the invention has a clamp with a releasable latch disposed about the resilient member. The clamp is selectively movable between an open position wherein the inner diameter of the resilient member is substantially unaffected, a clamp position wherein the clamp causes a strain to the resilient member and thereby reduces the inner diameter of the opening through the resilient member. The clamp also has a latch position where the latch releasably retains the clamp in the clamp position.

19 Claims, 8 Drawing Sheets

VARIABLE EXTENSION COMBINED SPINAL/EPIDURAL NEEDLE SET AND METHOD FOR ITS USE

FIELD OF INVENTION

The present invention is generally related to the field of hypodermic needles and more specifically to hypodermic needles intended for administration and withdrawal of fluids to the spine of a patient.

BACKGROUND

Generally speaking, there are two basic techniques for introducing injectable medicament into the spinal area of a patient. The techniques both can be used to create spinal anesthesia, one being delivery of the medicament into the epidural space, "epidural," and the other, penetration of the dural membrane with delivery of the medicament into the subarachnoid space, "spinal" or "subarachnoid." The medicaments can be any type of liquid therapeutic material including antibiotics, steroids and the like, but generally are agents used for anesthesia and analgesia. When the liquid medicament is an anesthetic agent, a subarachnoid placement is recognized as providing a faster, more uniform distribution, but several major side effects may result from an improper subarachnoid placement. These side effects may include nerve damage, either from contact with the needle or from high local concentrations of the medicament, pooling or inadequate mixing of the medicament in the cerebrospinal fluid.

Delivery of the medicament into the subarachnoid space requires a penetration depth of several centimeters. Puncture of the dural membrane for introduction of a needle or catheter with a large gauge needle may result in postoperative leakage of cerebrospinal fluid from the puncture site, often resulting in severe postoperative headaches. Thus, when puncture of the dural membrane is made with a needle, the smaller the size of the puncture the lower the probability of post-procedural leakage of cerebrospinal fluid. Small diameter needles of the length required to enter the subarachnoid space are quite flexible and as a result, difficult to accurately position when making penetrations to a depth of several centimeters. Practitioners have recognized the need to use a needle with sufficient stiffness to make the initial penetration and the need to use a small diameter needle for penetration of the dural membrane. This recognition has evolved into the use of an eight to ten centimeters long, larger diameter (ca. 16–18 gauge) introducer needle to enter the epidural space followed by the use of the bore of the introducer needle to place a longer, i.e., twelve to sixteen centimeters long, smaller diameter (ca. 22–28 gauge) spinal needle adjacent to and then to penetrate the dural membrane. The spinal needle is then used to administer a bolus of the anesthetic agent. The bolus results in rapid onset of anesthesia, and depending upon the placement and the amount administered, the effect may last several hours.

Correct placement and delivery of a subarachnoid medicament is recognized by practitioners as being one of the more technique sensitive procedures currently practiced. There is considerable anatomical variation between patients related to the patient's size and weight. The practitioner generally positions the introducer needle between the vertebrae into the epidural space adjacent the dural membrane (dura), then advances the spinal needle through the dura membrane into the subarachnoid space. Accurately perceiving when the dura has been penetrated is often difficult for the practitioner. There are several widely practiced techniques to confirm that the needle has entered the subarachnoid space. Some practitioners depend upon feeling a "pop" as the spinal needle penetrates the dura. Other practitioners routinely place a drop of fluid on the proximal hub of the spinal needle and depend upon observing the drop being drawn into the hub when the dura is penetrated. Many practitioners also often confirm that the subarachnoid space is penetrated by using the spinal needle to withdraw a sample of cerebrospinal fluid.

A survey of previous patent literature reports in this general area is found in U.S. Pat. No. 5,085,631. The patent discloses a method for placement of a subarachnoid catheter that utilizes a three component apparatus comprising an outer needle, an inner needle and a catheter intermediate the two needles.

A recent U.S. pat., No. 5,312,375, discloses a set for spinal anesthesia that includes a spinal needle, a stylet, an introducer needle through which the spinal needle is introduced and a clamp for fixing the spinal needle for fixing the spinal needle to the introducer needle to stabilize the spinal needle. The patent teaches that the tube portion of the introducer needle protrudes proximally beyond the introducer needle hub so that a regulating device with a thumb screw or a toothed member can engage both the introducer needle and the spinal needle to fix the position of the spinal needle relative to the introducer needle. Generally, the introducer needle is an epidural needle. As disclosed in U.S. Pat. No. 5,312,375, the introducer needle cannot function as a conventional epidural needle, because the fluid path of the epidural needle is not fluid tight to a fluid handling attachment at the hub of the needle.

U.S. Pat. No. 5,584,820, discloses a variant of the regulating device disclosed in U.S. Pat. No. 5,312,375 for adjusting the length of a combined spinal epidural needle and the method of practicing its use. The disclosed invention utilizes standard commercially available spinal and epidural needles, adding a fixture for preselecting the spinal needle projection with respect to the epidural needle when the spinal needle is coaxially placed within the epidural needle. While this regulating device and method may be quite useful in the practice of combined spinal epidural medication, the use of this device disclosed in U.S. Pat. No. 5,584,820 adds an additional item to the procedure kit, and additional manipulations. Additionally, neither of these variants teach that the attachment between the spinal needle and the epidural needle forms a fluid tight seal, thus, leakage of medicament or cerebrospinal fluid between the spinal needle and the epidural needle may occur.

Subarachnoid placement of medicaments, if done properly, is recognized as desirable. Thus, a device and a method for its use that would minimize the size of the puncture of the dural membrane, allow accurate and controlled placement of a therapeutically effective amount of a medicament within the subarachnoid space, thereby reducing the potential for nerve damage, coupled with an ability to rapidly initiate and maintain a therapeutic level of the medicament for longer procedures would represent an advance to the medical arts. If such an epidural needle that facilitated the subarachnoid placement that was fully functional as a standard epidural needle the art would be further advanced. A method and apparatus that addresses these needs constitute the present invention.

SUMMARY

An epidural needle of the present invention includes a hollow bore therethrough and is useful for releasably fixing a position of a spinal needle disposed within the bore of the epidural needle. The epidural needle of the invention has an elongate tube defining a longitudinal axis having a proximal end, a distal end and an axial hollow bore having an inside diameter therethrough. The needle has a hub with a proximal end, a distal end and an open passageway having an inside diameter substantially similar to the hollow bore therethrough, the distal end of the hub being fixedly attached to the proximal end of the elongate tube so that the hollow bore of the elongate tube is in fluid communication and substantial axial alignment with the open passageway. The hub further has a cavity disposed between the proximal end and the distal end of the hub. There is a resilient member with an opening therethrough that has an inner diameter substantially similar to the inside diameter of the hollow bore disposed in the cavity so that the opening is substantially axially aligned and in fluid communication with the open passageway. The hub of the epidural needle of the invention has a clamp with a releasable latch disposed about the resilient member. The clamp is selectively movable between an open position wherein the inner diameter of the resilient member is substantially unaffected, a clamp position wherein the clamp causes a strain to the resilient member and thereby reduces the inner diameter of the opening through the resilient member. The clamp also has a latch position where the latch releasably retains the clamp in the clamp position. Thus, a practitioner using the epidural needle of the invention to position a spinal needle with an outside diameter less than the inside diameter of the hollow tube may freely axially move the spinal needle within the hollow bore with respect to the epidural needle and fix a position of the spinal needle relative to the epidural needle by the reduction of the inner diameter opening through the resilient member to a diameter less than the outside diameter of the spinal needle by movement of the clamp to the clamp position and the latch position.

The epidural needle of the invention is easily manipulated by the practitioner to position the spinal needle. Additionally, the epidural needle of the invention is fully functional as a standard epidural needle since the fluid path from the needle bore to the hub is fluid tight. The projection of the spinal needle relative to the epidural needle is substantially infinitely variable within the full range of projection and, once the desired position is achieved, easily fixed by engaging the clamp on the resilient member. Until the clamp is engaged, a practitioner does not need to alter practices used with a standard epidural needle and a standard spinal needle. The engagement of the clamp to fix the position of the spinal needle relative to the epidural needle is facile and substantially intuitive. The invention provides an advance to the art of delivery of medicaments to the subarachnoid space.

BRIEF DESCRIPTION OF THE DRAWINGS

FIG. 5a is a cross-sectional view of the epidural needle of the invention taken from FIG. 2 along the line 5a—5a;

DETAILED DESCRIPTION

Figure 1:
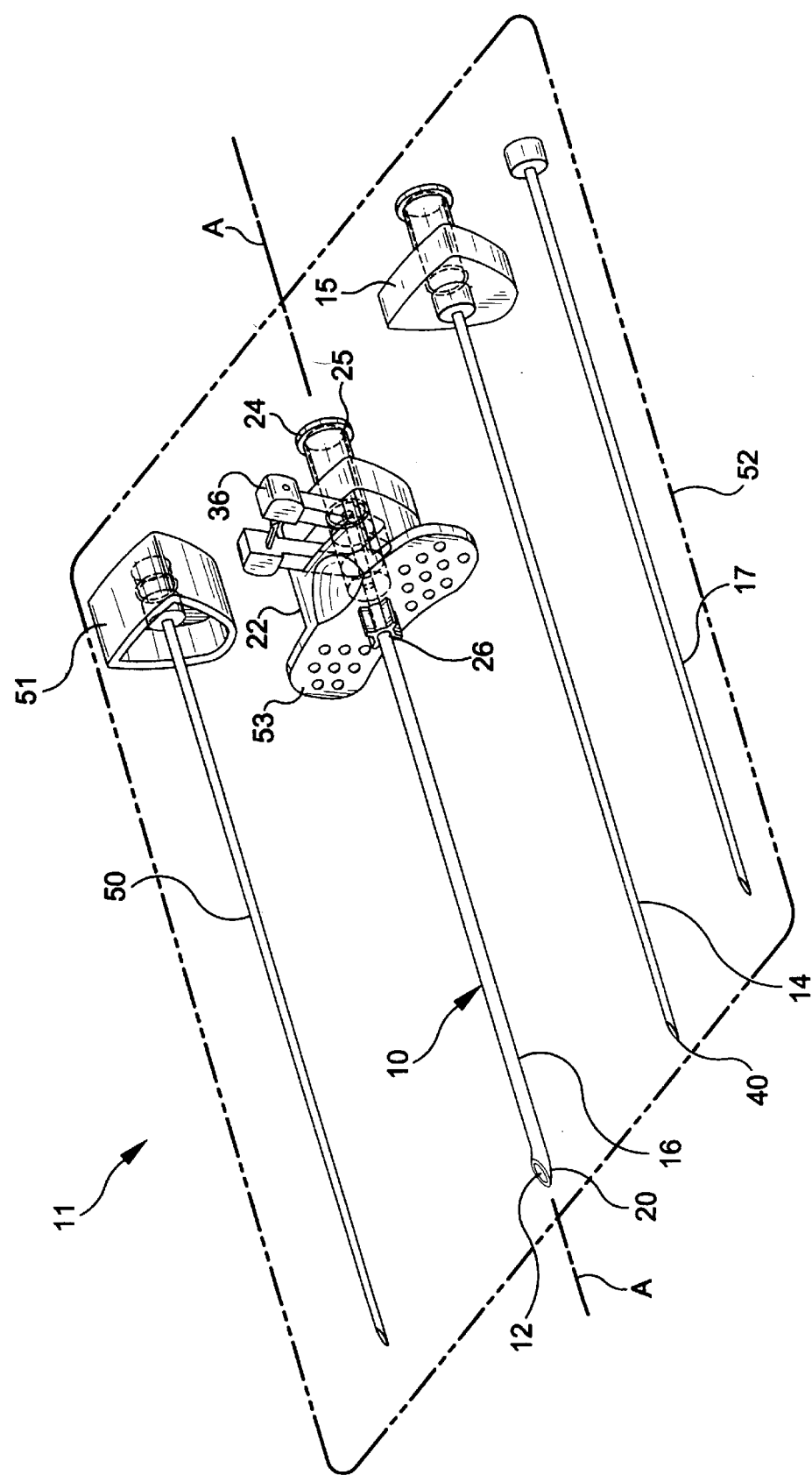
FIG. 1 is a perspective view of the epidural needle of the invention in a kit including other elements.

While this invention is satisfied by embodiments in many different forms, there is shown in the drawings and herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents. For the purposes of this description of the present invention, the term "distal end" refers to the end of the assembly closest to the needle point and the patient, whereas the term "proximal end" refers to the end of the assembly furthest from the needle point and closest to the practitioner.

Referring to FIGS. 1–7, an epidural needle 10 of the present invention includes a hollow bore 12 therethrough and is useful for releasably fixing a position of a spinal needle 14 disposed within bore 12 of the epidural needle. Spinal needle 14 has a proximal hub 15. Epidural needle 10 of the invention has an elongate tube 16 defining a longitudinal axis "A" having a proximal end 18, a distal end 20 and axial hollow bore 12 having an inside diameter "b" therethrough. Needle 10 has a hub 22 with a proximal end 24, a distal end 26 and an open passageway 28 having an inside diameter substantially similar to inside diameter "b" of hollow bore 12 therethrough. Distal end 26 of hub 22 is fixedly attached to proximal end 18 of elongate tube 16 so that hollow bore 12 of elongate tube 16 is in fluid communication and substantial axial alignment with open passageway 28. Hub 22 further has a cavity 30 disposed between proximal end 24 and distal end 26 of the hub. There is a resilient member 32 with an opening 34 therethrough that has an inner diameter "d" substantially similar to inside diameter "b" of hollow bore 12 disposed in cavity 30 so that opening 34 in the resilient member is substantially axially aligned and in fluid communication with open passageway 28. Hub 22 of epidural needle 10 of the invention has a clamp 36 with a releasable latch 38 disposed about resilient member 32. Clamp 36 is selectively movable between an open position, best seen in FIG. 5a, wherein inner diameter "d" of resilient member opening 34 is substantially unaffectecd, a clamp position, best seen in FIG. 5b, wherein clamp 36 causes a strain to resilient member 32 and thereby reduces the inner diameter of opening 34 through the resilient member. Clamp 36 also has a latch position, best seen in FIG. 5b, where latch 38 releasably retains clamp 36 in the clamp position. Thus, a practitioner using epidural needle 10 of the invention to position spinal needle 14 with an outside diameter "e" less than the inside diameter "b" of hollow bore 12 may freely axially move spinal needle 14 within the hollow bore with respect to epidural needle 10 and fix a position of a distal point 40 of spinal needle 14 relative to epidural needle 10 by the reduction of inner diameter "d" of opening 34 through resilient member 32 to a diameter "d'" less than outside diameter "e" of spinal needle 14 by movement of clamp 36 to the clamp position and the latch position. The design of clamp 36 is provided to illustrate, but not limit, the invention. Other designs for clamp 36 which cause sufficient strain on resilient member 32 to reduce inside diameter "b" sufficiently to fix the position of the spinal needle may be envisioned and are considered within the scope of the invention.

Figure 2:
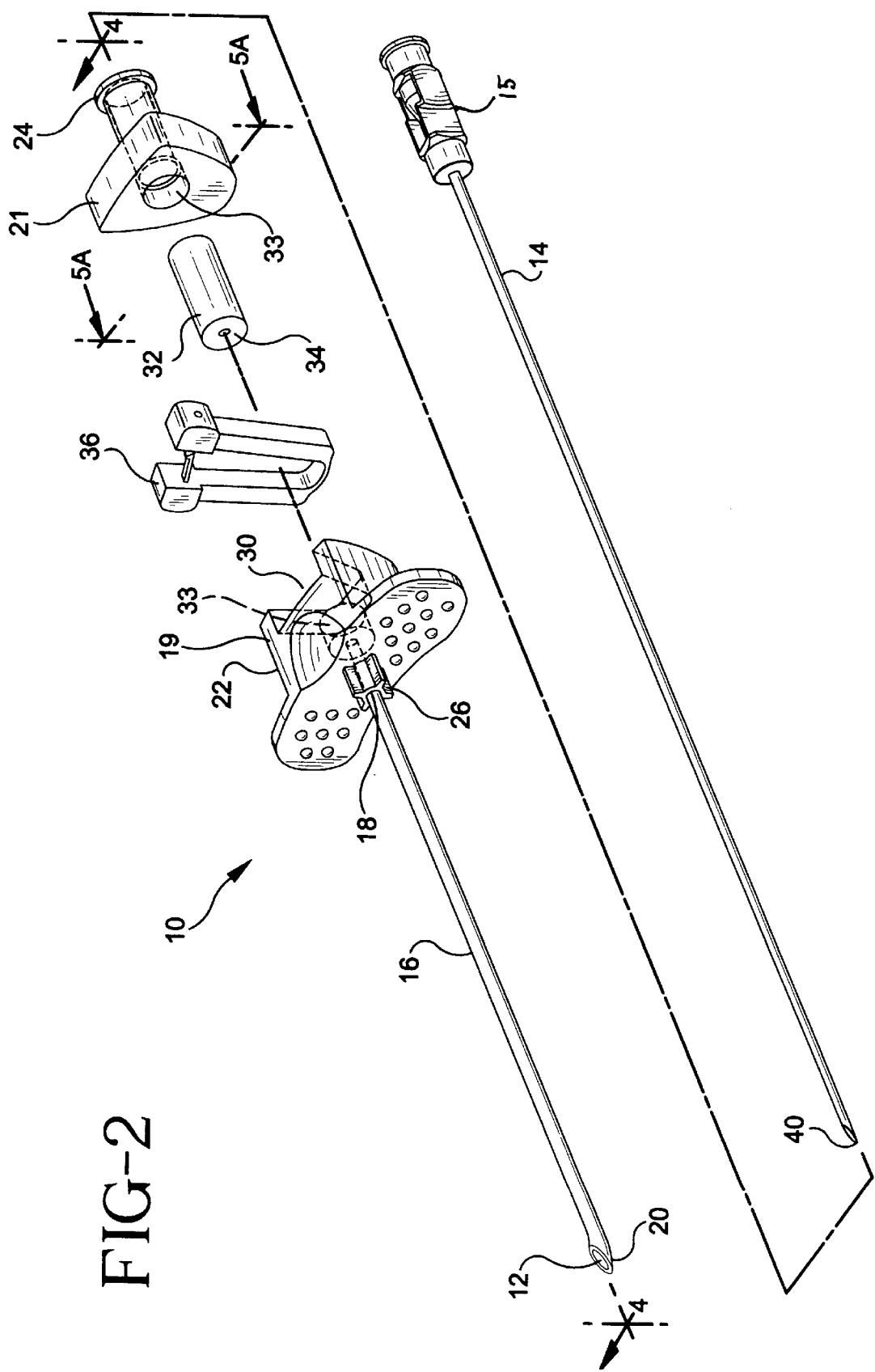
FIG. 2 is partially exploded perspective view of the epidural needle of FIG. 1.
Figure 3:
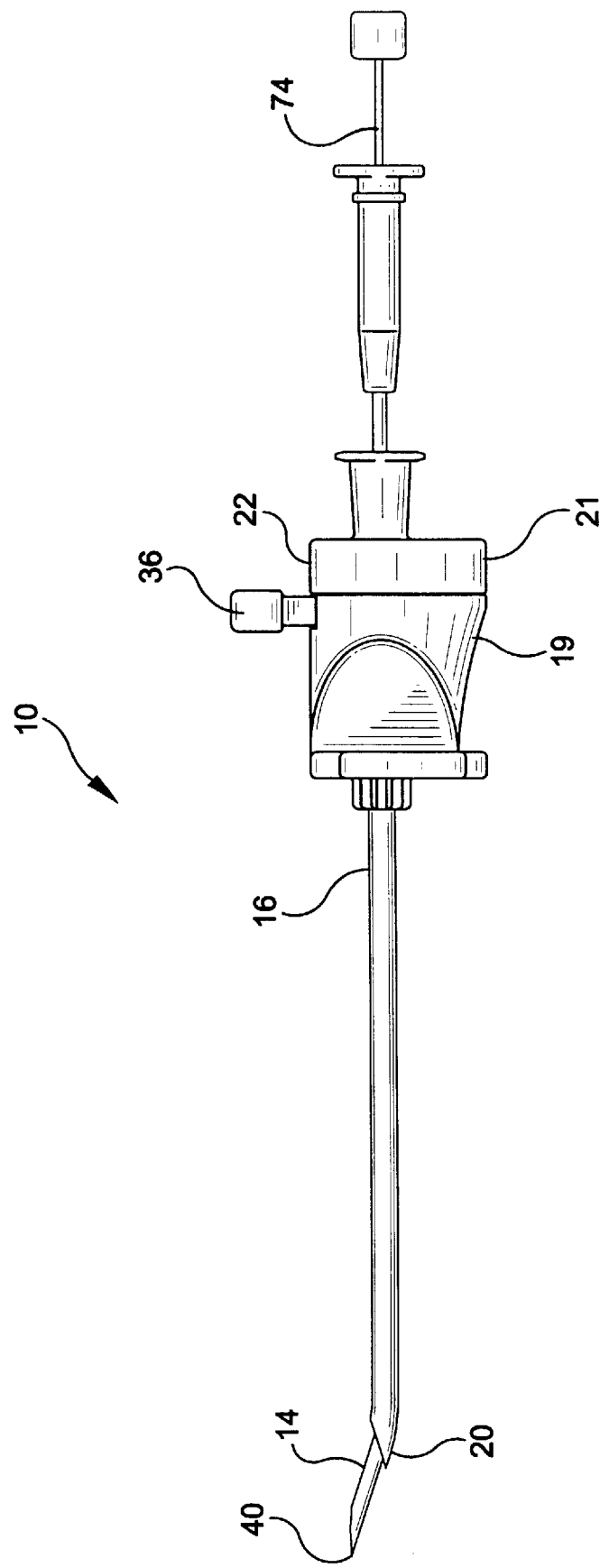
FIG. 3 is a side elevation of the invention of FIG. 1 with a spinal needle positioned in the hollow bore of the needle.
Figure 4:
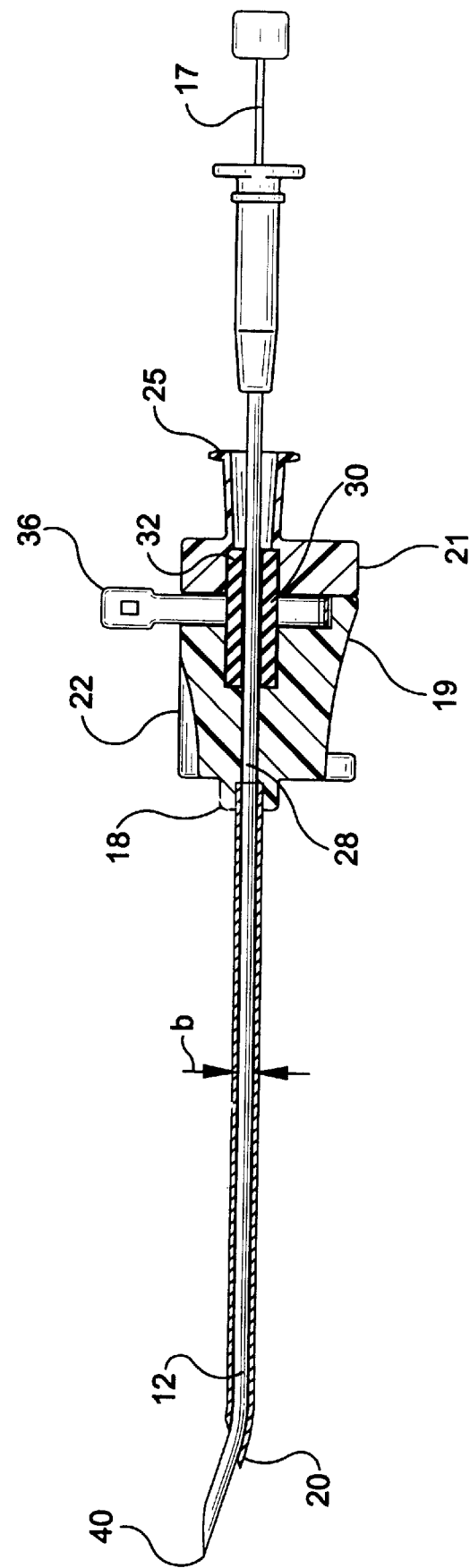
FIG. 4 is a horizontal cross-sectional view of the invention taken from FIG. 3 along the line 4—4.
Figure 5A:
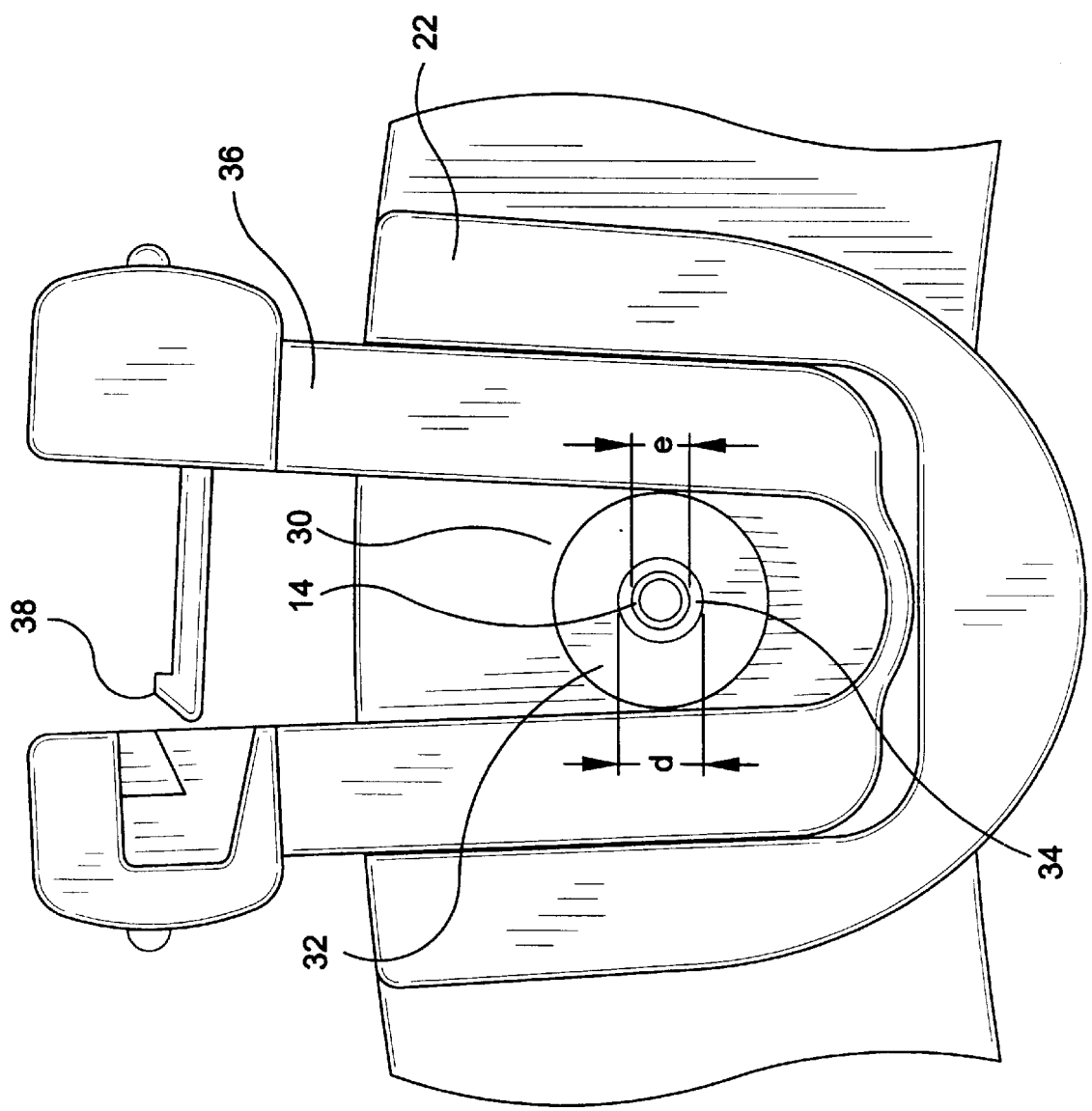
Figure 5B:
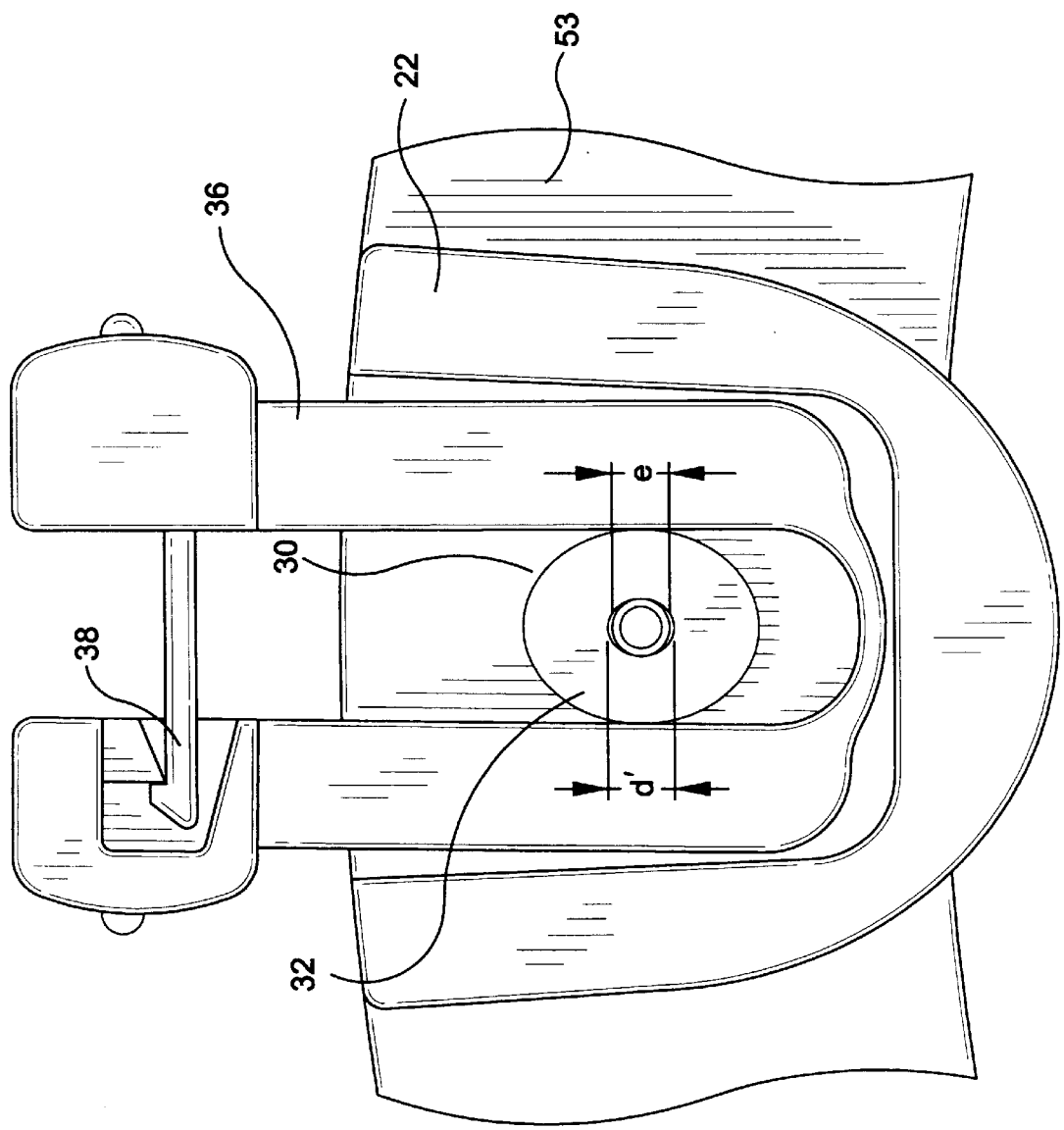
FIG. 5b is a cross-sectional view of the epidural needle of the invention, analogous to FIG. 5a, illustrating the clamp in the clamping position.

As best seen in FIG. 1, hub 22 of the epidural needle and a hub 51 of stylet 50 preferably are shaped to facilitate the practitioner's handling. For particular applications, hub 15 of spinal needle 14 may also have a similar shape, as shown in FIG. 1, or a more conventional shape as shown in FIG. 2. Hub 22 also preferably includes wings 53, which preferably are fixedly attached to the hub, but may be removable for particular applications. Proximal end 24 of hub 22 also includes an attachment for a fluid handling device, preferably a female luer fitting 25.

Preferably, hub 22 is formed in two portions, a distal portion 19 and a proximal portion 21 that are joined together after placement of resilient member 32 with clamp 36 into cavity 30. Distal portion 19 and proximal portion 21 may be joined together by snap fit, adhesive bonding, solvent bonding, thermal welding, sonic welding or other techniques for fixedly attaching parts formed from thermoplastic materials. Preferably, the parts are joined by solvent bonding. Preferably, proximal portion 21 and distal portion 19 each define part of cavity 30 and each include a recess 33 shaped to form a substantially fluid tight seal about resilient member 30 so that hollow bore 12 of the needle is in substantially fluid tight communication with preferred female luer fitting 25. Since resilient member 32 forms a substantially fluid tight seal between bore 12 and female luer fitting 25, epidural needle 10 is fully suitable for any procedure, including, but not limited to, use with a loss of resistance syringe and hanging drop procedure, normally practiced with standard epidural needles in addition to the disclosed ability to fix the position of a spinal needle with respect to the epidural needle. This versatility of use is not possible with previous variable extension spinal/epidural devices.

Preferably, epidural needle 10 is part of a kit 11 that includes spinal needle 14 and a stylet 50 to occlude hollow bore 12 of the epidural needle and placed in a package 52, illustrated in phantom in FIG. 1. Kit 11 may also include a stylet 17 for spinal needle 14. Kit 11 may also include other items (not shown) in addition to spinal needle 14 and stylet 17, such as gloves, skin preparation materials, medicaments and the like for particular applications.

Package 52 is preferably formed from materials substantially resistant to microorganisms, sealed and exposed to conditions suitable to render any microorganisms therein non-viable. Suitable materials for forming package 52 include but are not limited to thermoplastic films, metallic foils, paper, non-wovens as well as combinations of these materials. Suitable conditions for rendering microorganisms non-viable include, but are not limited to, exposure to gaseous agents such as ethylene oxide, vapor phase hydrogen peroxide and the like, and exposure to ionizing radiation such as is generated by electron beam, ultraviolet or gamma radiation Resilient member 32 is preferably formed from a resilient elastomeric material. Suitable elastomeric materials include, but are not limited to, natural rubber, synthetic rubber, silicone elastomer, ethylene propylene diene monomer (EPDM) and the like. Preferably, a resilient material is selected with a Shore A durometer between about 30 and 80 to be formed into resilient member 32. In these figures resilient member 32 is shown as a cylinder, other elongate shapes also are considered within the scope of the disclosure and may be selected for particular applications.

Suitable materials for forming hub 22 include, but are not limited to, thermoplastic resins such as polypropylene, polyethylene, polycarbonate, polystyrene and the like. Generally, it is preferable to form elongate tube 16 from a metallic material such as a stainless steel. Preferably, elongate tube 16 is fixedly attached to hub 22 by an adhesive bond, but other known methods of bonding including, but not limited to, insert molding and the like may be used for particular applications. Preferably, distal point 20 of epidural needle 10 is formed into a sharpened point suitable for penetrating a patient's tissue.

Figure 6:
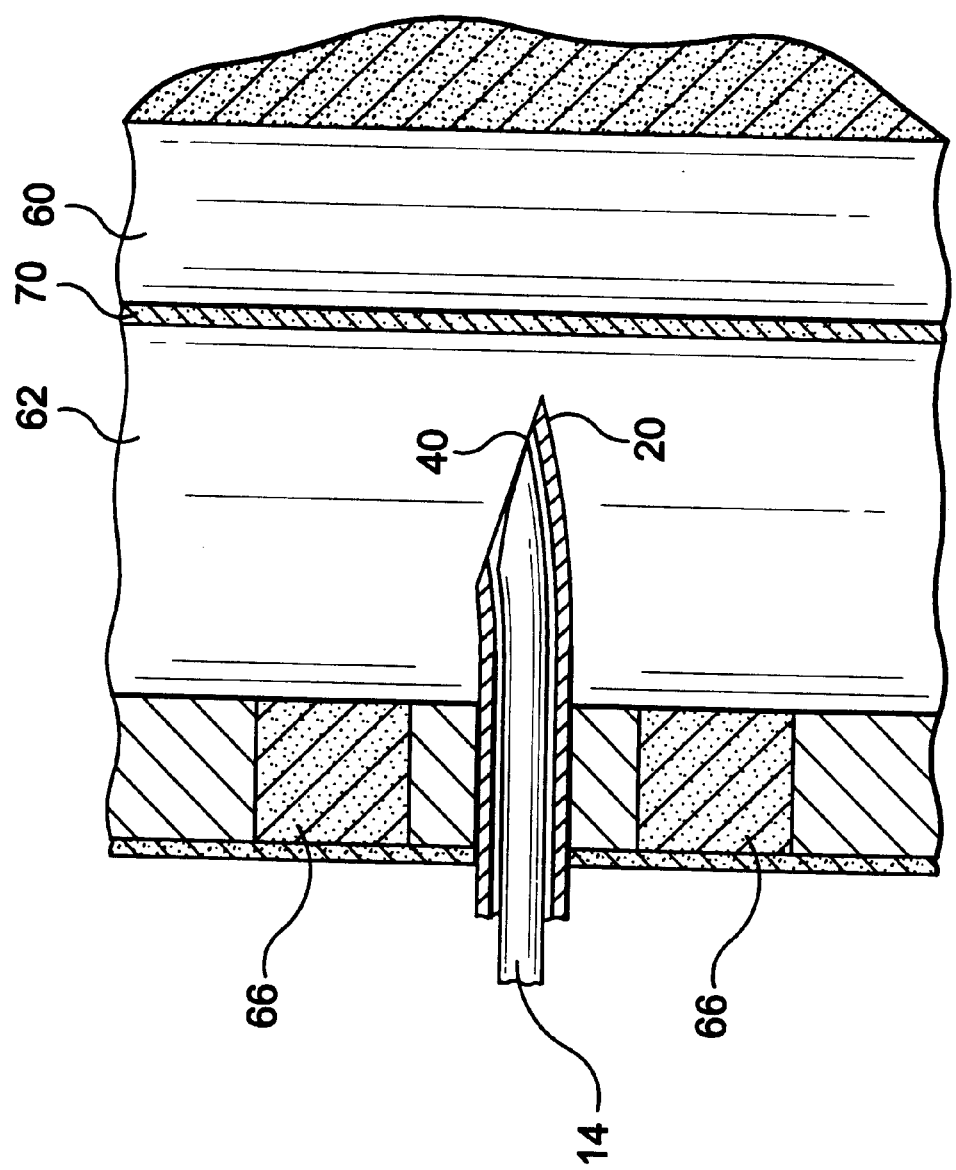
FIG. 6 is a schematic cross-sectional view of a portion of the human spine penetrated by the invention of FIG. 1.
Figure 7:
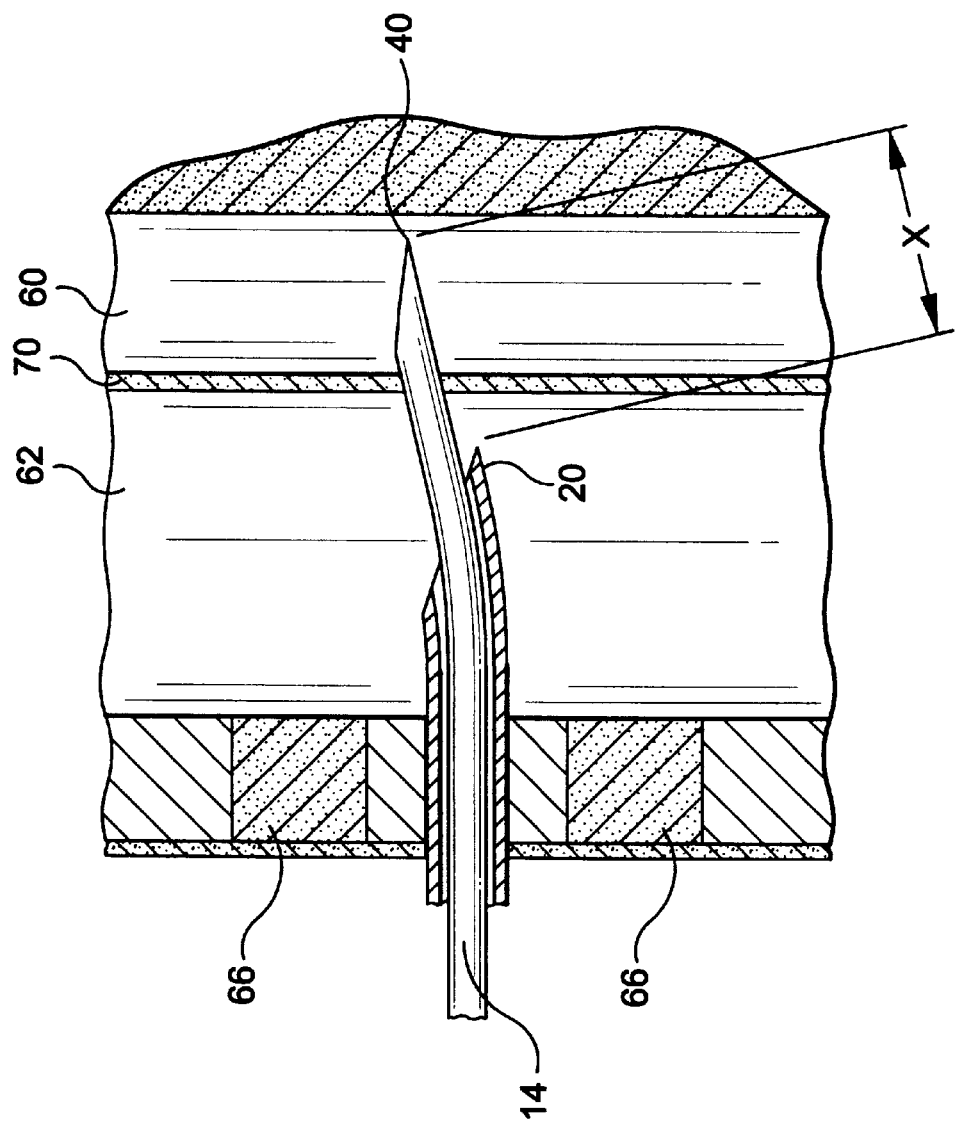
FIG. 7 is a schematic cross-sectional view of the portion of the human spine illustrated in FIG. 6 with a spinal needle projecting a distance from the distal end of the epidural needle of the invention.

Referring to FIGS. 6 and 7, that illustrate a schematic cross section of a patient's spine 62, a method for a practitioner to use epidural needle 10 to position spinal needle 12 in the subarachnoid space 60 includes positioning epidural needle 10 in the lumbar region 64 of spine 62 between the vertebrae 66 so that distal point 20 of the epidural needle is in close proximity to the dural membrane 70. Preferably, epidural needle bore 12 is occluded by stylet 50 during the penetration of the needle through the patient's tissue so that no tissue core is cut, forced into bore 12 and possibly introduced into the patient's spine by the instillation of the medicament. To complete and confirm the placement of epidural needle 10 in the epidural space, the practitioner withdraws stylet 50 from bore 12 and then may attach a "loss of resistance" syringe containing normal saline solution or air. The practitioner then advances epidural needle 10 while applying pressure to the syringe plunger. Upon penetration into the epidural space, the practitioner perceives a "loss of resistance" to movement of the syringe plunger and the syringe contents are delivered into the now created epidural space. Following this, the practitioner removes the "loss of resistance" syringe and introduces spinal needle 14 into bore 12.

Epidural needle 10 of the invention, by having resilient member 32 form a substantially air and fluid tight seal between bore 12 of the needle and attachment 24 for a fluid handling device, allows the practitioner to use epidural needle 10 as a conventional needle for performing the "loss of resistance test". Earlier variable extension needles such as disclosed in U.S. Pat. No. 5,584,820 do not allow such use, because there is no fluid tight seal between the bore of the needle and a fluid attachment.

The practitioner preferably leaves clamp 36 in the open position to allow slidable movement of spinal needle 14 through bore 12. Spinal needle 14 preferably has indicia 15 to indicate the position of distal point 40 of the spinal needle is relative to distal point 20 of the epidural needle. The practitioner then advances epidural needle point 20 to close proximity to the dural membrane 70 and advances the spinal needle until the distal point 40 penetrates the dural membrane and enters subarachnoid space 60. The practitioner then may move clamp 36 to the clamp position and engage latch 38 to fix the position of the spinal needle relative to the epidural needle with a projection distance "X". Preferably, latch 38 of clamp 36 is selectively engageable and releasable by the practitioner to accommodate the practitioner's needs during the procedure. Spinal needle 14 may also include a removable stylet 17 to occlude the bore of the spinal needle until the practitioner has completed the placement of spinal needle 14. Once placement of spinal needle 14 in the subarachnoid space is achieved and confirmed, the practitioner then may attach a fluid handling device such as a syringe to the spinal needle and instill the medicament into the subarachnoid space.

The table below relates standard needle gauge sizes to the inner and outer diameter of hypodermic tubing used for forming the needles described above.

Table of Hypodermic Tubing Nominal Sizes

| Gauge | Outside Diameter (mm) | Inside Diameter (mm) |
| --- | --- | --- |
| 30 | 0.30 | 0.18 |
| 29 | 0.33 | 0.20 |
| 28 | 0.36 | 0.20 |
| 27 | 0.40 | 0.25 |
| 26 | 0.46 | 0.30 |
| 25 | 0.51 | 0.30 |
| 24 | 0.56 | 0.36 |
| 23 | 0.64 | 0.38 |
| 22 | 0.71 | 0.46 |
| 21 | 0.82 | 0.56 |
| 20 | 0.90 | 0.65 |
| 19 | 1.08 | 0.80 |
| 18 | 1.27 | 0.96 |
| 17 | 1.50 | 1.17 |
| 16 | 1.65 | 1.32 |

Referring to the table of nominal needle gauge sizes above, the preferred needle set of the invention includes a twenty-five gauge spinal needle 14 slidably fit within a seventeen gauge epidural needle 0. Alternatively, a combination of a twenty-seven gauge spinal needle 14 and an eighteen gauge epidural needle 10, a twenty-seven gauge spinal needle 14 and a seventeen gauge epidural needle 10 or a twenty-nine gauge spinal needle 14 and an eighteen gauge epidural needle 10 or other similar combinations may be preferred for particular applications and are considered within the scope of the invention. The larger number gauge size (smaller outside diameters) combinations are often preferred for patients of smaller stature or for pediatric applications. Spinal needles 14 having gauge sizes between about twenty-two gauge and twenty-nine gauge are preferred by most practitioners for most applications. Useful needle length ranges accommodative of most patient statures include epidural needle 10 having an effective penetration length between about 8 cm to about 9 cm and spinal needle 14 having a sufficient length so that projection distance ("X") of spinal needle point 40 beyond epidural needle point 20 when the spinal needle is fully seated in epidural needle 10 is between about 14.5 mm to about 15.5 mm. For particular applications other lengths of both the spinal and epidural needles may be preferred. In general, consideration of a number of factors including, but not limited to, the desired spinal needle projection ("X") range and the patient stature range should be considered when selecting design parameters including, but not limited to, gauge sizes, needle lengths and the particular configuration of the projection adjustment mechanism for the invention. Numerous other combinations of these design parameters beyond those described in this disclosure may be envisioned and are considered to be within the scope of the invention.

Epidural needle 10 provides practitioners an improvement in their ability to deliver medicaments to the subarachnoid space. Since epidural needle 10 provides a fluid tight and unrestricted path between bore 12 and attachment 24 as long as clamp 36 is not engaged, the epidural needle of the invention is suitable for any normal procedure that may be desired by the practitioner. The epidural needle of the invention then provides the practitioner to fix the position of the spinal needle with respect to the epidural needle. The epidural needle of the invention in combination with a standard spinal needle or a preferred spinal needle having a hub shape similar to the preferred shape of the epidural needle hub is easy to use and allows the practitioner more control of the penetration of the dural membrane than currently available needle sets. By providing the practitioner with more control, the needle set of the invention substantially reduces the chance of adverse effects on the patient receiving the treatment.

What is claimed is:

1. An epidural needle having a hollow bore therethrough useful for releasably fixing a position of a spinal needle disposed within the bore of the epidural needle comprises:

an elongate tube defining a longitudinal axis having a proximal end, a distal end and an axial hollow bore having an inside diameter therethrough;

a hub having a proximal end, a distal end and an open passageway having an inside diameter substantially similar to said hollow bore therethrough, said distal end of said hub being fixedly attached to said proximal end of said elongate tube so that said hollow bore of said elongate tube is in fluid communication and substantial axial alignment with said open passageway, said hub further having a cavity therein disposed between said proximal end and said distal end of said hub;

a resilient member having an opening therethrough with an inner diameter, substantially similar to said inside diameter of said hollow bore, said resilient member disposed in said cavity so that said opening is substantially axially aligned and in fluid communication with said open passageway; and a clamp having a releasable latch disposed about said resilient member, said clamp being selectively movable between an open position wherein said inner diameter of said resilient member is substantially unaffected, a clamp position wherein said clamp causes a strain to at least a portion of said resilient member thereby reducing said inner diameter of said opening through at least a portion of said resilient member, and a latch position wherein said latch releasably retains said clamp in said clamp position; and wherein a practitioner using said epidural needle to position a spinal needle having an outside diameter less than said inside diameter of said hollow tube may freely axially move the spinal needle within said hollow bore with respect to said epidural needle and fix a position of the spinal needle relative to said epidural needle by said reduction of said inner diameter of said opening through said resilient member to a diameter less than the outside diameter of the spinal needle by movement of said clamp to said clamp position and said latch position thereby to grasp releasably the spinal needle sufficiently to fix the relative position of the spinal needle.

2. The epidural needle of claim 1 wherein said distal end of said elongate tube comprises a point suitable for penetration of mammalian tissue.

3. The epidural needle of claim 1 wherein said at least a portion of said clamp projects outwardly from said hub to facilitate the practitioner's selective movement of said clamp between said open position, said clamp position and said latch position.

4. The epidural needle of claim 3 wherein said portion of said clamp that projects outwardly from said hub is sized and shaped to allow the practitioner to apply digital pressure for said selective movement of said clamp between said open position, said clamp position and said latch position.

5. The epidural needle of claim 4 wherein said portion of said clamp that projects outwardly from said hub further includes said releasable latch for selectively retaining said clamp in said clamp position.

6. The epidural needle of claim 1 wherein said hub further includes at least one outwardly projecting wing substantially transverse to said axis, said at least one wing being useful to facilitate the practitioner's placement of said epidural needle.

7. The epidural needle of claim 1 wherein said resilient member is formed from a resilient material selected from the group consisting of natural rubber, synthetic rubber, silicone rubber, polyurethane and ethylene propylene diene monomer (EPDM).

8. The epidural needle of claim 7 wherein said resilient material has a Shore A durometer between about 30 and about 80.

9. The epidural needle of claim 7 wherein said resilient member forms a substantially air and fluid tight seal between said epidural needle hub and an outside surface of said spinal needle when said clamp is positioned in said clamp position and said latch position.

10. The epidural needle of claim 1 wherein said proximal end of said hub further comprises an attachment for a fluid handling device.

11. The epidural needle of claim 10, wherein said resilient member is disposed in said hub so that said bore of said epidural needle is in substantially fluid tight communication with said attachment for said fluid handling device.

12. The epidural needle of claim 10 wherein said attachment for the fluid handling device comprises a female luer fitting.

13. The epidural needle of claim 1 wherein said hub further comprises a first portion and a second portion, said portions being joined together after placement of said resilient member in said cavity.

14. A method for releasably fixing a position of a spinal needle disposed within the bore of an epidural needle comprises:

providing an epidural needle including an elongate tube defining a longitudinal axis, said tube having a proximal end, a distal end and an axial hollow bore having an inside diameter therethrough, a hub having a proximal end, a distal end and an open passageway having an inside diameter substantially similar to said hollow bore therethrough, said distal end of said hub being fixedly attached to said proximal end of said elongate tube so that said hollow bore of said elongate tube is in fluid communication and substantial axial alignment with said open passageway and wherein said open hub further having a cavity disposed between said proximal end and said distal end of said hub, a resilient member having an opening therethrough with an inner diameter, substantially similar to said inside diameter of said hollow bore, said resilient member disposed in said cavity so that said opening is substantially axially aligned and in fluid communication with said open passageway, and a clamp having a releasable latch disposed about said resilient member, said clamp being selectively movable between an open position wherein said inner diameter of said resilient member is substantially unaffected, a clamp position wherein said clamp causes a strain to said resilient member thereby reducing said inner diameter of said opening through said resilient member, and a latch position wherein said latch releasably retains said clamp in said clamp position;

placing a spinal needle having an outside diameter less than said inside diameter of within said hollow bore of said epidural needle;

selecting a position of said spinal needle relative to said epidural needle; and fixing a position of said spinal needle relative to said epidural needle by moving of said clamp to said clamp position and said latch position thereby releasably fixing said position of said spinal needle relative to said epidural needle.

15. A combined spinal epidural needle set comprises:

an epidural needle including an elongate tube defining a longitudinal axis having a proximal end, a distal end and an axial hollow bore having an inside diameter therethrough, said epidural needle having a hub having a proximal end, a distal end and an open passageway having an inside diameter substantially similar to said hollow bore therethrough, said distal end of said hub being fixedly attached to said proximal end of said elongate tube so that said hollow bore of said elongate tube is in fluid communication and substantial axial alignment with said open passageway and wherein said hub further having a cavity disposed between said proximal end and said distal end of said hub, a resilient member having an opening therethrough with an inner diameter, substantially similar to said inside diameter of said hollow bore, said resilient member disposed in said cavity so that said opening is substantially axially aligned and in fluid communication with said open passageway, and a clamp having a releasable latch disposed about said resilient member, said clamp being selectively movable between an open position wherein said inner diameter of said resilient member is substantially unaffected, a clamp position wherein said clamp causes a strain to said resilient member thereby reducing said inner diameter of said opening through said resilient member, and a latch position wherein said latch releasably retains said clamp in said clamp position; and a spinal needle having an outside diameter less than said inside diameter of said hollow tube disposed within said hollow bore, and wherein a practitioner using said epidural needle to position said spinal needle may freely axially move said spinal needle within said hollow bore with respect to said epidural needle and fix a position of said spinal needle relative to said epidural needle by said reduction of said inner diameter opening through said resilient member to a diameter less than said outside diameter of the spinal needle by movement of said clamp to said clamp position and said latch position thereby to grasp releasably the spinal needle sufficiently to fix the position.

16. The combined spinal epidural needle set of claim 15 further comprising a stylet sized and shaped to fit removably within and substantially occlude said hollow bore of said epidural needle.

17. The combined spinal epidural needle set of claim 15 further comprising a stylet sized and shaped to fit removably within and substantially occlude a bore of said spinal needle.

18. The combined spinal epidural needle set of claim 17 wherein each of said hub of said epidural needle, a hub of said spinal needle, a hub of said epidural needle stylet and a hub of said spinal needle stylet have a size and shape and are disposed to be engaged with one another to facilitate a practitioner's manipulation of said set during a procedure.

19. The combined spinal epidural needle set of claim 15 being placed in a package formed from materials substantially resistant to the passage of microorganisms and exposed to conditions that render substantially any microorganisms inside said package non-viable.

* * * * *